United States Patent
van Oort et al.

(10) Patent No.: US 10,808,499 B2
(45) Date of Patent: Oct. 20, 2020

(54) HYDROCARBON DETECTION IN OIL AND GAS WELLS USING FIBER OPTIC SENSING CABLES

(71) Applicant: Board of Regents, The University of Texas System, Austin, TX (US)

(72) Inventors: Eric van Oort, Bee Cave, TX (US); Qian Wu, Austin, TX (US); Sriramya Duddukuri Nair, Austin, TX (US); Michelle Shuck, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 528 days.

(21) Appl. No.: 15/355,597

(22) Filed: Nov. 18, 2016

(65) Prior Publication Data

US 2017/0139076 A1     May 18, 2017

Related U.S. Application Data

(60) Provisional application No. 62/256,949, filed on Nov. 18, 2015.

(51) Int. Cl.
*E21B 33/14* (2006.01)
*G01L 1/24* (2006.01)
(Continued)

(52) U.S. Cl.
CPC ............ *E21B 33/14* (2013.01); *E21B 47/005* (2020.05); *E21B 47/07* (2020.05); *E21B 47/113* (2020.05);
(Continued)

(58) Field of Classification Search
CPC ............................. E21B 47/0005; E21B 47/123
See application file for complete search history.

(56) References Cited

U.S. PATENT DOCUMENTS

| 4,386,269 | A | 5/1983 | Murphy et al. |
| 4,927,232 | A | 5/1990 | Griffiths et al. |

(Continued)

FOREIGN PATENT DOCUMENTS

WO     2015127109 A1     8/2015

OTHER PUBLICATIONS

Buerck, et al., "Distributed Fiber Optical HC Leakage and pH Sensing Techniques for Implementation into Smart Structures", (2004), doi:10.1117/12.538240.

(Continued)

*Primary Examiner* — Herbert K Roberts
(74) *Attorney, Agent, or Firm* — Kilpatrick Townsend & Stockton LLP

(57) ABSTRACT

Methods and systems that provide ways to detect the hydrocarbon flow while eliminating the hydrogen darkening effect in the downhole environment by separated strain and temperature measurement. The methods and systems use fiber optic sensing cables for real-time detection of hydrocarbon fluids (oil, gas, condensate or combination) in oil and gas wells, for example in cemented annuli between either a rock formation and a casing string, or between a larger diameter casing string and a smaller diameter casing string, or in a cement plug left in the well upon abandonment. Hydrogen darkening-resistant temperature and strain sensing fiber optic cables can be used in conjunction with hydrocarbon sensitive polymers to monitor hydrocarbon migration in the oil and gas well and/or to identify the zone(s) from which the hydrocarbons are flowing.

42 Claims, 8 Drawing Sheets

(51) Int. Cl.
*G01D 5/353* (2006.01)
*G01K 11/32* (2006.01)
*G01N 21/88* (2006.01)
*E21B 47/005* (2012.01)
*E21B 47/07* (2012.01)
*E21B 47/113* (2012.01)
*E21B 47/135* (2012.01)
*G01N 33/38* (2006.01)

(52) U.S. Cl.
CPC ....... *E21B 47/135* (2020.05); *G01D 5/35316* (2013.01); *G01K 11/3206* (2013.01); *G01L 1/246* (2013.01); *G01N 21/88* (2013.01); *G01K 2011/322* (2013.01); *G01K 2011/324* (2013.01); *G01N 33/383* (2013.01)

(56) References Cited

U.S. PATENT DOCUMENTS

| | | | |
|---|---|---|---|
| 5,015,843 | A | 5/1991 | Seitz et al. |
| 6,753,520 | B2 | 6/2004 | Spirin et al. |
| 7,548,681 | B2 | 6/2009 | Rubinstein et al. |
| 7,561,776 | B2 | 7/2009 | Chalifoux et al. |
| 7,769,251 | B2 | 8/2010 | Varkey et al. |
| 8,111,960 | B2 | 2/2012 | Dowd et al. |
| 8,640,527 | B2 | 2/2014 | Hara et al. |
| 8,776,609 | B2 | 7/2014 | Dria et al. |
| 2003/0094281 | A1* | 5/2003 | Tubel .................. E21B 47/135 166/250.03 |
| 2004/0047534 | A1 | 3/2004 | Shah et al. |
| 2011/0308788 | A1* | 12/2011 | Ravi .................. E21B 33/14 166/250.01 |
| 2012/0076464 | A1 | 3/2012 | Dowd et al. |
| 2012/0205103 | A1* | 8/2012 | Ravi .................. E21B 33/14 166/285 |
| 2017/0260848 | A1* | 9/2017 | Xia .................. E21B 47/107 |
| 2018/0238167 | A1* | 8/2018 | Ravi .................. G01V 1/226 |

OTHER PUBLICATIONS

Buerck, et al., "OTDR Fiber-Optical Chemical Sensor System for Detection and Location of Hydrocarbon Leakage", J Hazard Mater. (2003), 102(1):13-28.

Carrillo, et al., "New Distributed Optical Sensor for Detection and Localization of Liquid Leaks: Part I. Experimental Studies", Sensors and Actuators A 99 (2002) 229-235.

Lopez, et al., "Coherent Optical Frequency Domain Reflectometry for Interrogation of Bend-Based Fiber Optic Hydrocarbon Sensors", Optical Fiber Technology (2004), 10 (1): 79-90.

Lopez, et al., "Fiber Optic Distributed Sensor for Hydrocarbon Leak Localization Based on Transmission/reflection Measurement", Optics & Laser Technology (2002), 34 (6): 465-69.

Maclean, et al., "Detection of Hydrocarbon Fuel Spills Using a Distributed Fiber Optic Sensor", Sensors and Actuators A: Physical 109 (2003), (1-2): 60-67.

Maclean, et al., "Distributed Fiber Optic Sensors for Humidity and Hydrocarbon Detection", (2000), doi:10.1117/12.388123.

International Preliminary Report on Patentability issued in International Application No. PCT/US2016/062675, dated May 31, 2018.

International Search Report and Written Opinion issued in International Application No. PCT/US2016/062675, dated Jan. 30, 2017.

* cited by examiner

HYDROCARBON DETECTION IN OIL AND GAS WELLS USING FIBER OPTIC SENSING CABLES

FIELD

The disclosed devices and methods have utility in the field of petroleum engineering, particularly with regard to monitoring the integrity of the cement sheath and state of zonal isolation of an oil or natural gas well.

BACKGROUND

In the process of finishing a borehole section drilled in an oil or natural gas well, a cement sheath may be placed between the wellbore and the casing that is put in place to secure the section. After the cementing operation, the cement sheath is expected to provide zonal isolation in the well (for instance to prevent leaking of the formation fluids out of any hydrocarbon reservoirs behind the casing and into non-reservoir zones at different locations along the oil or gas well), and to avoid any uncontrolled migration/flow of formation fluids to the surface. The cement sheath is expected to provide this safeguard for the life of the well, i.e., for an indefinite period. However, during the cementing operation, incomplete displacement of drilling fluids by cement might lead to defects like voids in the cement annulus. Moreover, temperature and pressure variations, compressive and tensile loads in the casing or other factors in the complicated downhole environment that are present during drilling and production operations can cause cracking in the cement sheath during the life of the well, debonding of the cement from either the casing or the formation, or both. Once connected, these cracks and voids might become channels that provide paths for hydrocarbon migration and communication between different zones. All of these issues related to poor cementing can compromise the integrity of the well, shortening the productive life of the well, necessitating costly remedial and well abandonment work, and increasing the risk of well control incidents that could result in loss of life, economical loss, and environmental damage. One particular concern is that such defects in poor cementations may connect hydrocarbon reservoirs with shallow aquifers that are used for drinking water and other important water supply purposes.

There are currently no sensors available that can reliably and continuously assess the state of zonal isolation in an oil and gas well. Moreover, the sensor techniques that have been developed require active entry into the well using drillpipe (drillpipe-conveyed logging) or wireline (wireline logging) to deploy sensor and logging tools. This (re-)entry is a costly proposition, as it requires, e.g., suspending production on an actively producing well, mobilizing people and equipment, and time and costs involved with all operations, as well as additional risks due to potential well control incidents (e.g. blowouts caused during such well intervention).

SUMMARY

The methods and systems disclosed herein provide ways to detect any hydrocarbon migration or flow while at the same time eliminating the hydrogen darkening effect that often complicates fiber optic sensor measurements. The disclosed methods and systems use sensing cables for real-time detection of hydrocarbon fluids (oil, gas, condensate or combination) in oil and gas wells, for example in cemented annuli between either a rock formation and a casing string, or between a larger diameter casing string and a smaller diameter casing string, or in a cement plug left in the well upon abandonment. The presence of hydrocarbon fluids in such annuli means that the cementation is compromised (e.g. cracked, fractured, de-bonded, or simply not present) and that zonal isolation may be jeopardized. The methods and systems can be used to monitor hydrocarbon migration in the oil and gas well and/or to identify the zone(s) from which the hydrocarbons are migrating or flowing in the actual downhole environment.

The disclosed hydrocarbon sensing fiber optic cables comprise optical fibers that are resistant to hydrogen darkening, used in combination with hydrocarbon sensitive polymers. The presence of unwanted hydrocarbons in the oil and gas well (e.g. in a cement annulus that has defects such as cracks, channel, or voids) causes the polymer around the fiber to swell, which in turn will cause a change in the strain on the fiber. These strain variations can be measured using any fiber optic sensing system. Furthermore, since hydrocarbons flowing from a different zone might have a different temperature than that of the oil and gas well itself, the temperature measured by the sensing cable can be used to identify the zone from which the hydrocarbons are flowing. The use of optical fibers with the ability to separate strain and temperature measurements facilitates device design, data collection and data processing.

Disclosed herein is a sensing cable for monitoring cement integrity and zonal isolation in a downhole environment. The sensing cable includes a hydrocarbon-sensitive polymer that undergoes a change in a physical property in the presence of hydrocarbons, and a hydrogen darkening-resistant optical fiber connected to the hydrocarbon-sensitive polymer such that a change in a physical property of the hydrocarbon-sensitive polymer produces a change in a measurable property of the optical fiber. The optical fiber is capable of separating strain and temperature measurements.

The optical fiber comprises a hydrogen darkening-resistant material. For example, the core of the optical fiber can be pure silica core or fluorine-doped silica, or the optical fiber can have a carbon coating. The optical fiber can be single mode, multimode, or a combination of single and multimode.

In some embodiments, the physical property of the hydrocarbon-sensitive polymer that changes in the presence of hydrocarbons is the degree of swelling. The change in the degree of swelling produces a change in the strain on the optical fiber. The hydrocarbon-sensitive polymer can be in direct contact with the optical fiber, or the swelling of the polymer can be transmitted through an intermediate material. Hydrocarbon-sensitive polymer materials can include natural rubber and synthetic rubber, such as silicone rubber, butyl rubber or EPDM rubber.

The sensing cable can include a packaging configured to reinforce the optical fiber. The packaging includes a protective outer sheath surrounding the optical fiber and the hydrocarbon-sensitive polymer. The packaging can also include a rigid and bendable reinforcement rod running through the protective outer sheath. The reinforcement rod can be, for example, a fiberglass or steel material. In some implementations, the reinforcement rod is surrounded by the hydrocarbon-sensitive polymer, and the optical fiber is attached to the outer surface of the hydrocarbon-sensitive polymer. In some embodiments, the optical fiber is attached to the outer surface of the hydrocarbon-sensitive polymer using a helically wound Kevlar thread.

Also disclosed herein is a method of assessing cement integrity in a downhole environment in real time. The method includes attaching to a casing at least one sensing cable comprising a hydrogen darkening-resistant optical fiber and a hydrocarbon-sensitive polymer, positioning the casing in the downhole environment and adjacent to cement, measuring a change in a property of the optical fiber when there is a change in a physical property of the hydrocarbon-sensitive polymer, and thereby assessing cement integrity. The change in the physical property of the hydrocarbon-sensitive polymer is indicative of a factor that affects the integrity of the cement.

In some implementations, measuring a change in a property of the optical fiber comprises measuring the strain in the optical fiber when there is a change in the swelling of the hydrocarbon-sensitive polymer. Measuring the change in strain can be performed by calculating the Rayleigh scattering in the optical fiber, the Brillouin scattering in the optical fiber, or both Rayleigh and Brillouin scattering in the optical fiber. Raman scattering may also be calculated to account for temperature effects. In some implementations, both Rayleigh and Raman scattering may be calculated. In some implementations, both Brillouin and Raman scattering may be calculated. In some aspects of the method, different types of hydrocarbon-based contaminants can be differentiated by distinguishing the degree to which the physical property of the hydrocarbon-sensitive polymer is changed.

In some implementations, the temperature of the downhole environment can be measured with the same optical fiber that measures strain. In other implementations, a second hydrogen-darkening resistant optical fiber can be included as part of the sensing cable, and the temperature of the downhole environment can be measured with the second optical fiber. The optical fiber of the methods disclosed herein can be a distributed fiber or a quasi-distributed optical fiber. For example, a quasi-distributed optical fiber can include one or more fiber Bragg gratings.

Assessing cement integrity can include assessing zonal isolation. It does not require re-entry into the well, and can occur continuously without interruption. In some implementations, assessing cement integrity can occur over long periods of time, for example, to monitor the quality of a permanent well abandonment. Assessing cement integrity can also include detecting hydrocarbon migration through the cement. Hydrocarbon origination zones can be identified to provide information for further remedial cementing steps. In some implementations, channels that provide paths for hydrocarbon migration can be detected. Assessing cement integrity can also include evaluating the state of primary cementation. This can be performed, for example, by monitoring heat evolution during cement hydration. Contamination of the cement with drilling fluids can also be detected by detecting variation in strain measurements, temperature measurements, or both.

The methods disclosed herein can further include attaching a plurality of sensing cables to the casing. The plurality can be oriented vertically along the casing, or they can be oriented at angles with the longitudinal axis of the casing. The angles that the individual cables make with the longitudinal axis can be the same, or they can be different. The methods may also include connecting the optical fiber to a surface read-out machine for measurement in the change in the property of the optical fiber. The surface read-out machine may be, for example, a hybrid Brillouin-Rayleigh distributed fiber optic sensing system.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several aspects of the disclosure, and together with the description, serve to explain the principles of the disclosure.

DETAILED DESCRIPTION

Figure 1A:
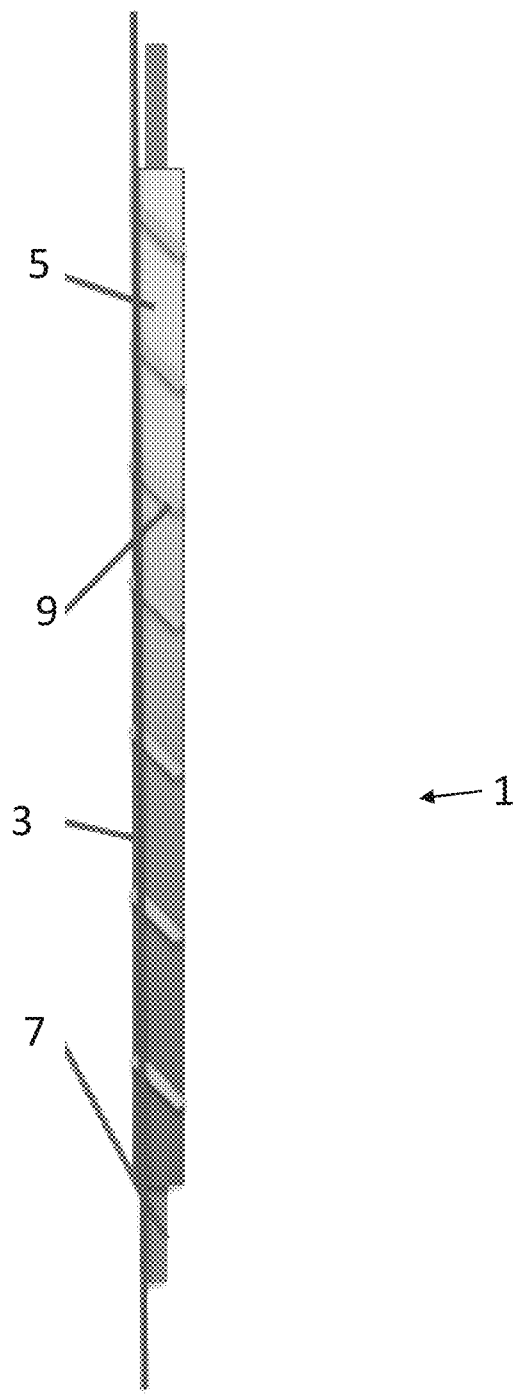
FIG. 1A is a schematic of a sensing cable.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about", it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to", and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Due to the material properties of hardened cement, it is very difficult to avoid cracking in the cement sheath, especially in the complicated downhole environment that exists during drilling, completion, hydraulic fracturing and production operations. Additionally, uncemented voids or other defects usually exist due to incomplete displacement of mud and spacer fluids with cement slurry. In some cases, these defects may not have a significant influence if they are not connected to create a path for any reservoir fluids migrating to other zones or to the surface. In such cases, remediation might not be required. However, when these cracks and voids are connected into channels and provide path(s) for hydrocarbons to migrate or flow, it can significantly affect the integrity of the well and lead to serious issues that may threaten the life of the well.

Most commonly used technologies to evaluate cement in the oil and gas industry are ultrasonic or acoustic logging tools, such as cement bond logging (CBL). Those logging technologies are conducted by running tools inside the well, which involves e.g. interruption of production operations if this occurs on a producing well. Note that these techniques also do not provide real-time, continuous monitoring capability, but instead present a snapshot of the well state at a specific moment of time; additional monitoring requires further re-entries into the well.

On the contrary, the sensing cables disclosed herein can always be in place, providing real-time, continuous monitoring of the state of zonal isolation without requiring costly, time-consuming (re-)entry into the well. Furthermore, once they are installed they can be used to conduct life-time monitoring, providing detailed information about the potential need for well intervention (e.g. remedial cementing jobs). The disclosed systems and methods may be particularly useful to ensure that the isolation systems (bridging devices, cement plugs, etc.) continue to provide zonal isolation during well abandonment. The sensing cable technology described herein can allow oil and gas operators to demonstrate (e.g. to regulators, public at large etc.) that they have indeed permanently abandoned their wells and maintain continuous control over any formation fluids (gas, oil, condensate, brine or a combination thereof) left in place.

Distributed fiber optic sensing systems used to evaluate the quality of a cement sheath have been available in recent years using fiber Bragg gratings, or FBG's (e.g. U.S. Pat. No. 8,776,609). This technology presents a method to monitor fluid migration by measuring both strain and temperature variations. However, this technology does not focus on detecting hydrocarbons in the cement sheath. Also, the fiber Bragg grating is currently the only fiber optic technology used, which requires Bragg gratings to be written on the fiber while at least two different fibers are required to achieve both temperature and strain measurement: one is strain-free for temperature only and the other one measures both temperature and strain.

Depending on the chemistry, the most common optical fibers have dopants in their silica cores like Germanium. When hydrocarbons flow through the wellbore and make contact with the optical fiber, some free hydrogen atoms are absorbed by the optical fiber and react with the dopants in its silica core, causing an irreversible increase in attenuation or loss of light, which is known as the hydrogen darkening effect. This effect can negatively affect the accuracy of the measurement. The higher the temperature, the faster the hydrogen darkening process. Thus, in high-temperature and high-pressure downhole environments, the hydrogen darkening effect becomes more significant and has a greater influence on the measurements of the fiber optic sensors.

The methods and systems disclosed herein provide ways to detect any hydrocarbon migration or flow while at the same time eliminating (or reducing) the hydrogen darkening effect that often complicates fiber optic sensors measurements. The disclosed methods and systems use sensing cables for real-time detection of hydrocarbon fluids (oil, gas, condensate or a combination thereof) in oil and gas wells, for example in cemented annuli between either a rock formation and a casing string, or between a larger diameter casing string and a smaller diameter casing string, or in a cement plug left in the well upon abandonment. The presence of hydrocarbons in such annuli means that the cementation is compromised (e.g. cracked, fractured, de-bonded, or simply not present) and that zonal isolation can be jeopardized. The methods and systems can be used to monitor hydrocarbon migration in the oil and gas well and/or to identify the zone(s) from which the hydrocarbons are flowing. In addition, the methods and systems can be also used to monitor the cement displacement process by tracking various well construction fluids and thus can be used to track their location in real time. In addition, due to the responses of the cables to various well construction fluids (such as synthetic-based drilling mud, spacer fluid) in different orders of magnitude, the system can be used to conduct real time cement displacement monitoring by tracking each of these fluids.

An example sensing cable 1 can be seen in FIG. 1A. The disclosed hydrocarbon sensing cables comprise optical fibers 3 that are resistant to hydrogen darkening, used in combination with hydrocarbon sensitive polymers 5. The presence of hydrocarbons in the oil and gas well (e.g. in a cement annulus that has defects such as cracks, channel or voids) causes the hydrocarbon-sensitive polymer 5 in contact with the optical fiber 3 to swell. This will in turn cause a change in the strain on the fiber. These strain variations can be measured using any fiber optic sensing system. Furthermore, since hydrocarbons flowing from a different zone might have a different temperature than that of the oil and gas well itself, the temperature measured by the sensing cable can be used to identify the zone from which the hydrocarbons are flowing. The use of optical fibers with the ability to separate strain and temperature measurements facilitates device design, data collection and data processing. Finally, the cable materials can be hydrogen darkening-resistant to reduce the problem of hydrogen darkening in the downhole environment.

Figure 1B:
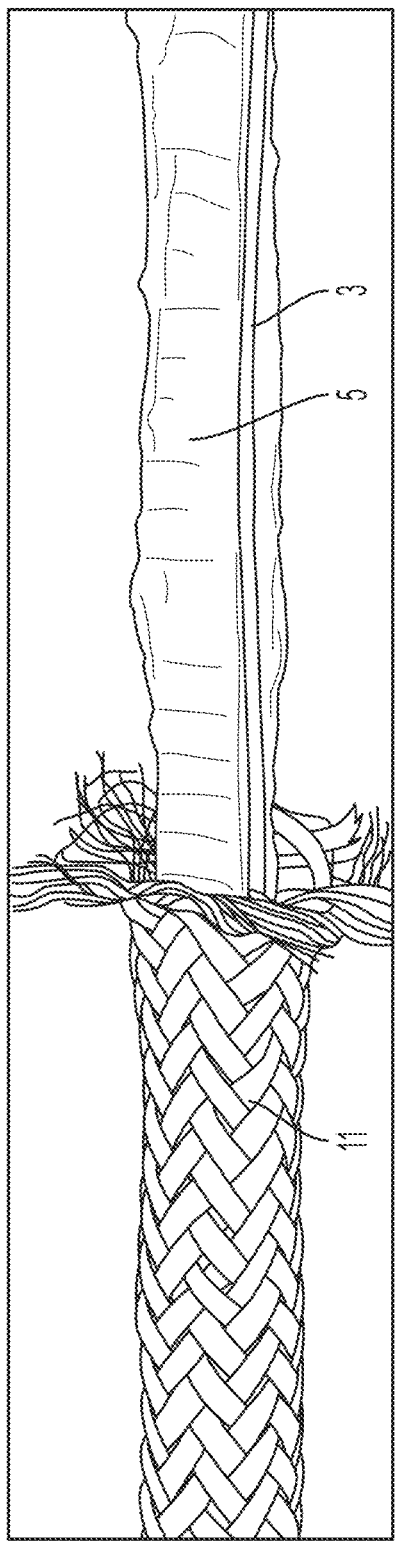
FIG. 1B is a photograph of a sensing cable partially covered by an outer sheath.

The sensing cable 1 for hydrocarbon detection includes at least one optical fiber 3 made of hydrogen darkening-resistant materials and coatings. The sensing cable also includes a hydrocarbon-sensitive polymer 5 that undergoes a change in a physical property, such as swelling, in the presence of hydrocarbons. As seen in FIG. 1B, the sensing cable can also include a packaging that protects the optical fiber while also ensuring that the hydrocarbon-sensitive polymer can respond to incoming hydrocarbons, or at least with volatile substances given off by hydrocarbons in the proximity. One or more sensing cables can be installed to the outside of the casing that goes into the wellbore, such that they are in proximity to the cement sheath of the wellbore.

The optical fiber 3 used in the sensing cable 1 can be single mode, multimode or the combination of both types depending on the type of optical fiber sensing technologies used. The chemistry of fiber core can be hydrogen darkening resistant. For example, the fiber core can be made up of pure silica or fluorine-doped silica. The coatings used for optical fiber 3 can provide additional protection for the fiber core from the hydrogen darkening effect. For example, the optical fiber 3 can have a carbon coating. However, for wells at lower temperature, the hydrogen darkening resistant materials may not be necessary. The composition of the fiber core, cladding, and coatings can be varied based on the locations and conditions of the well.

In one implementation, the optical fiber has the ability to separate temperature and strain measurements. For example, hybrid Brillouin-Rayleigh distributed fiber optic sensing systems can separate strain and temperature measurements using a single fiber. Other distributed fiber optic sensing systems involving Rayleigh, Brillouin, and Raman scattering, or quasi-distributed fiber optic sensing systems like fiber Bragg gratings (FBG) can also achieve separated temperature and strain measurements by using two fibers, where one strain-free fiber is for temperature measurement and the other measures both. Other methods used to separate temperature and strain measurements can also be considered.

The hydrocarbon-sensitive polymer 5 undergoes a change in a physical property in the presence of hydrocarbons. For example, the hydrocarbon-sensitive polymer 5 can be designed to swell in the presence of hydrocarbons. The swelling is then translated to strain within the optical fiber 3. The hydrocarbon-sensitive polymer can include natural rubber or synthetic rubber such as silicone rubber, butyl rubber, or ethylene propylene diene monomer (EPDM) rubber, for example. Other physical property changes that are able to be detected by the optical fiber 3 can also be considered.

Figure 1C:
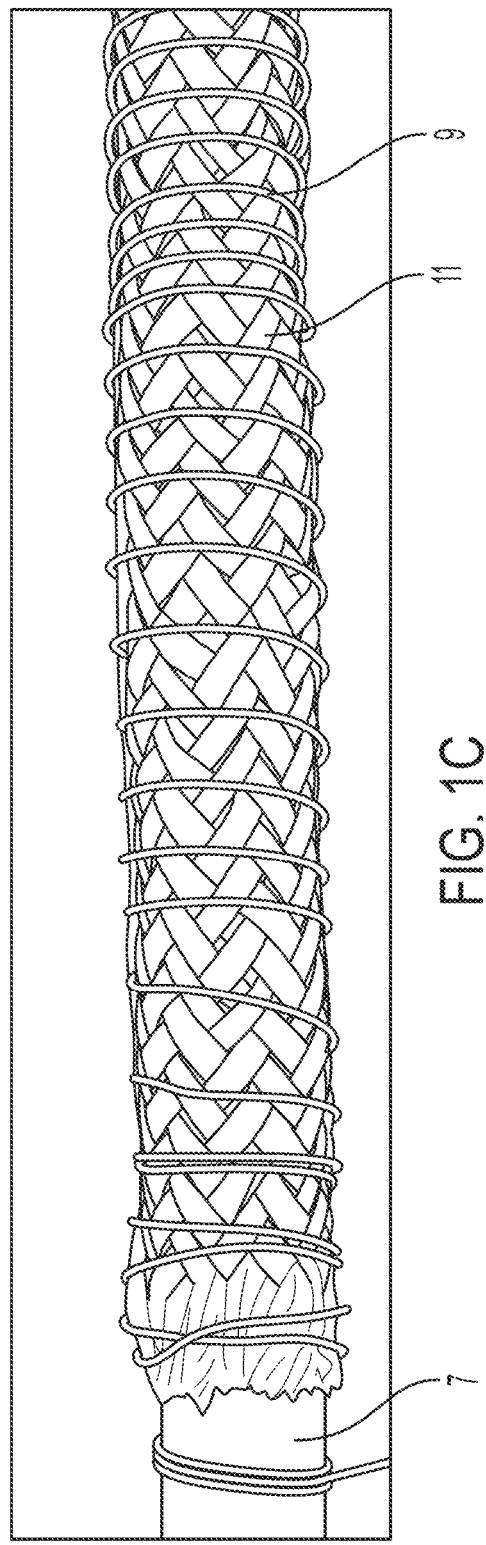
FIG. 1C is a photograph of a sensing cable covered by an outer sheath and wound by an attachment mechanism.

The packaging of the sensing cable protects the sensing cable and ensures that the physical property change of the hydrocarbon-sensitive polymer is detectable by the optical fiber. For example, if the physical property change is a swelling of the polymer, the packaging ensures that the fiber is in close enough proximity to be affected by the swelling. The packaging can include a reinforcement rod 7 and optionally, an outer sheath 11 as shown in FIG. 1B. The reinforcement rod 7 can be a rigid but bendable rod which can include materials such as fiberglass or steel. The reinforcement rod can be coated with the hydrocarbon-sensitive polymer 5. The optical fiber 3 can be attached to the reinforcement rod 7 and the hydrocarbon-sensitive polymer 5 using an attachment mechanism 9. For example, the attachment mechanism 9 can be a Kevlar thread wound helically around the optical fiber 3 and the outer surface of the hydrocarbon-sensitive polymer 5. The packaging can also include an outer sheath 11. In the example shown in FIG. 1B, the outer sheath 11 is a steel braid. In some implementations, such as the one shown in FIG. 1C, the attachment mechanisms 9 may be wound around the outer sheath 11, or there can be multiple attachment mechanisms running under and over the outer sheath 11.

One or more sensing cables can be installed on the casing vertically or helically at the same or varying angles depending on the applications. Using more cables can improve the reliability of the measurements. The change in the property of the optical fiber can be measured at the surface of the wellbore using a surface read-out machine. In one embodiment, the surface read-out machine may be a hybrid Brillouin-Rayleigh distributed fiber optic sensing system. Examples of commercially available fiber optic sensing systems that could be used as the surface read-out machine include DITEST STA-R™ from Omnisens, FORESIGHT™ from OZ Optics, Ltd., NEUBRESCOPE™ from Neubrex Co. Ltd., Optical Backscatter Reflectometer™ (OBR) from LUNA, Distributed temperature and strain sensor from Sensornet. However, other surface read-out machines and/or fiber optic sensing systems can also be considered.

When hydrocarbons flow into the cracks, voids or channels in the cement annulus or spaces between abandonment systems (e.g. bridge plugs, cement plugs) and make contact with the sensing cable, the hydrocarbon-sensitive polymer responds. This response is detected by the optical fiber. For example, a swelling of the hydrocarbon-sensitive polymer can be detected by strain variations on the optical fiber. The cement sheath is porous and is at times less than 1-in thick.

Even if the channels for hydrocarbon migration are not close to the sensing cables on the casing, volatile substances can still be detected through the porous cement sheath. The presence of hydrocarbons might also introduce temperature variations that can be measured by the sensing cable.

EXAMPLE

The cement sheath placed between a wellbore and a casing is expected to provide reliable zonal isolation throughout the life of a well. However, zonal isolation can be affected by several factors which can compromise cement integrity and lead to the development of channels that provide unwanted paths for hydrocarbons to flow. The sensing cable described herein is a real-time monitoring system for detecting issues with primary cementation and locating the presence of hydrocarbons in the cement sheath.

The sensing cable used in this example is a distributed temperature and strain sensing (DTSS) system, which is based on both Brillouin and Rayleigh scattering phenomena with the advantage of separating strain and temperature measurements using a single fiber. The sensing cable was used to detect hydrocarbons in the cement sheath. The cable comprises a single-mode optical fiber packaged along with a hydrocarbon-sensitive polymer and was tested with various hydrocarbons. Additionally, heat evolution of Portland cement contaminated with varying levels of synthetic-based mud (SBM), a drilling fluid, was also monitored using the DTSS system.

Figure 2:
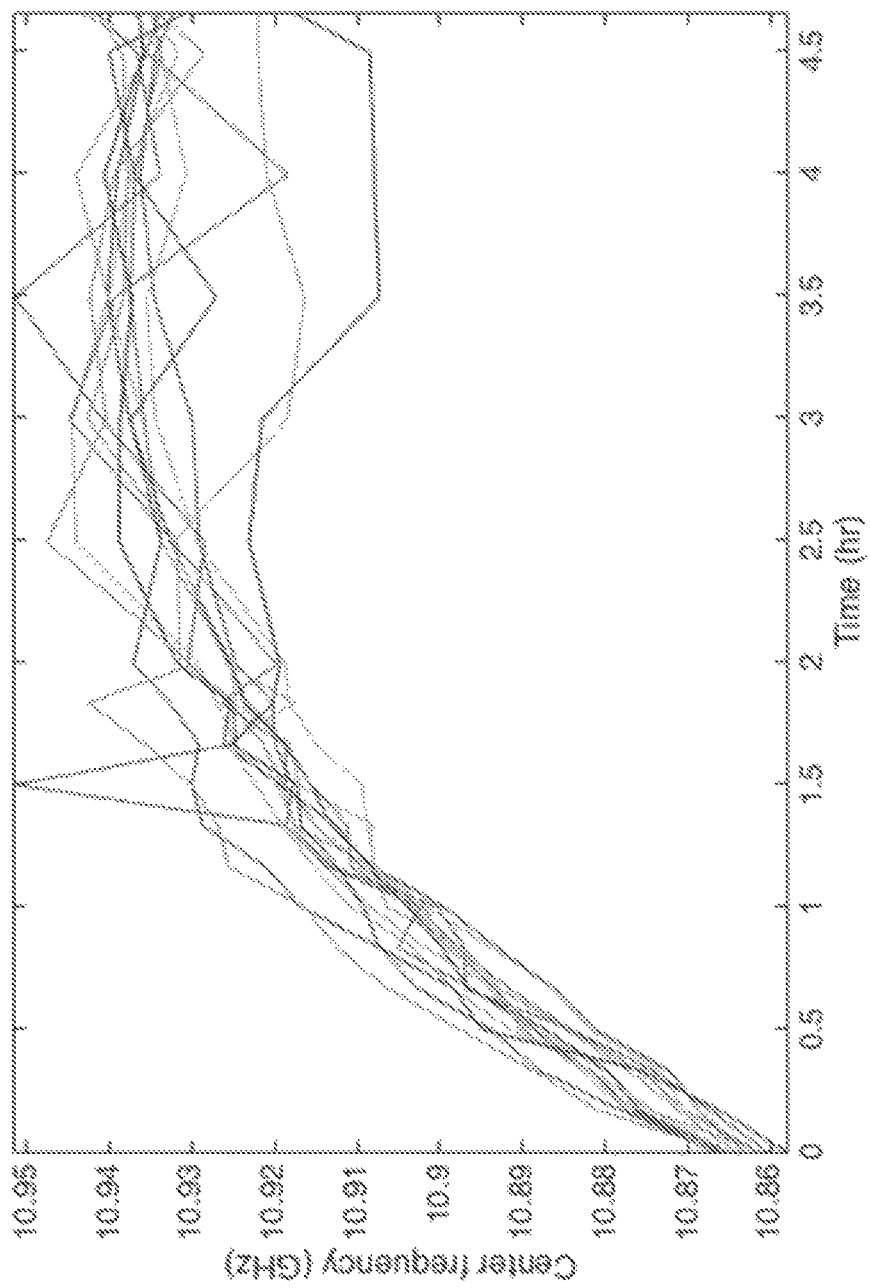
FIG. 2 is a line graph of the strain induced by the swelling hydrocarbon-sensitive polymer over time upon exposure to a hydrocarbon and at various points along the length of a sensing cable.
Figure 3A:
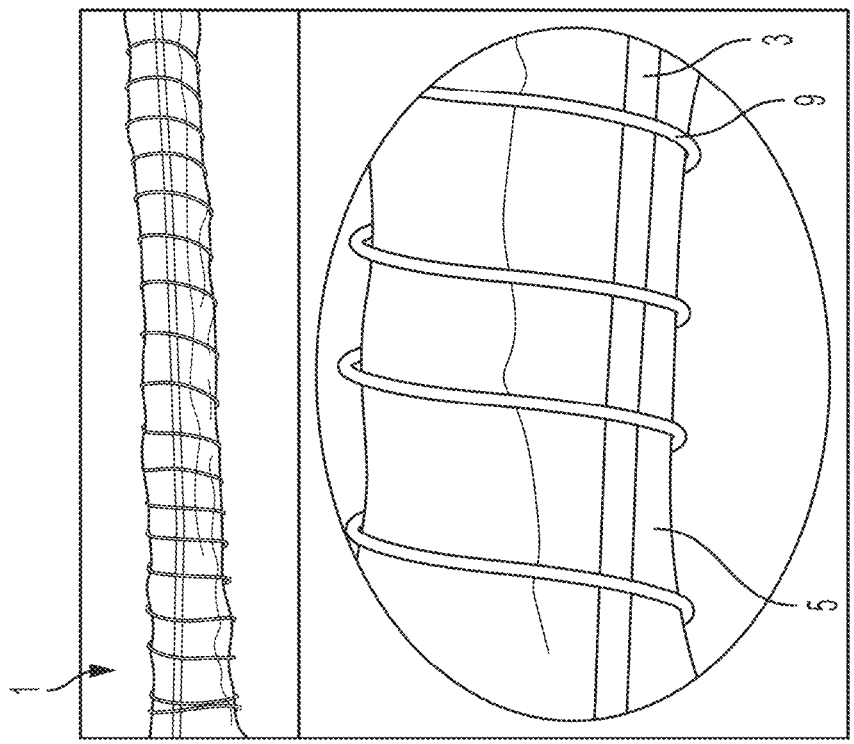
FIG. 3A is a photograph of a sensing cable after it has been exposed to a hydrocarbon. A magnified inset is provided.
Figure 3B:
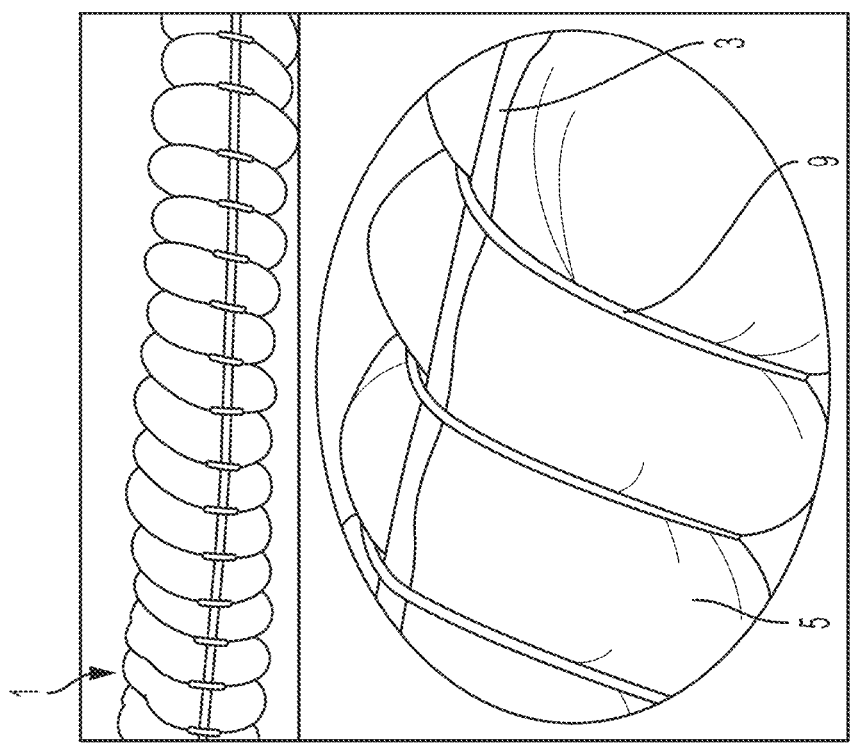
FIG. 3B is a photograph of the same sensing cable as FIG. 3A after discontinuation of the exposure to the hydrocarbon. A magnified inset is provided.
Figure 3C:
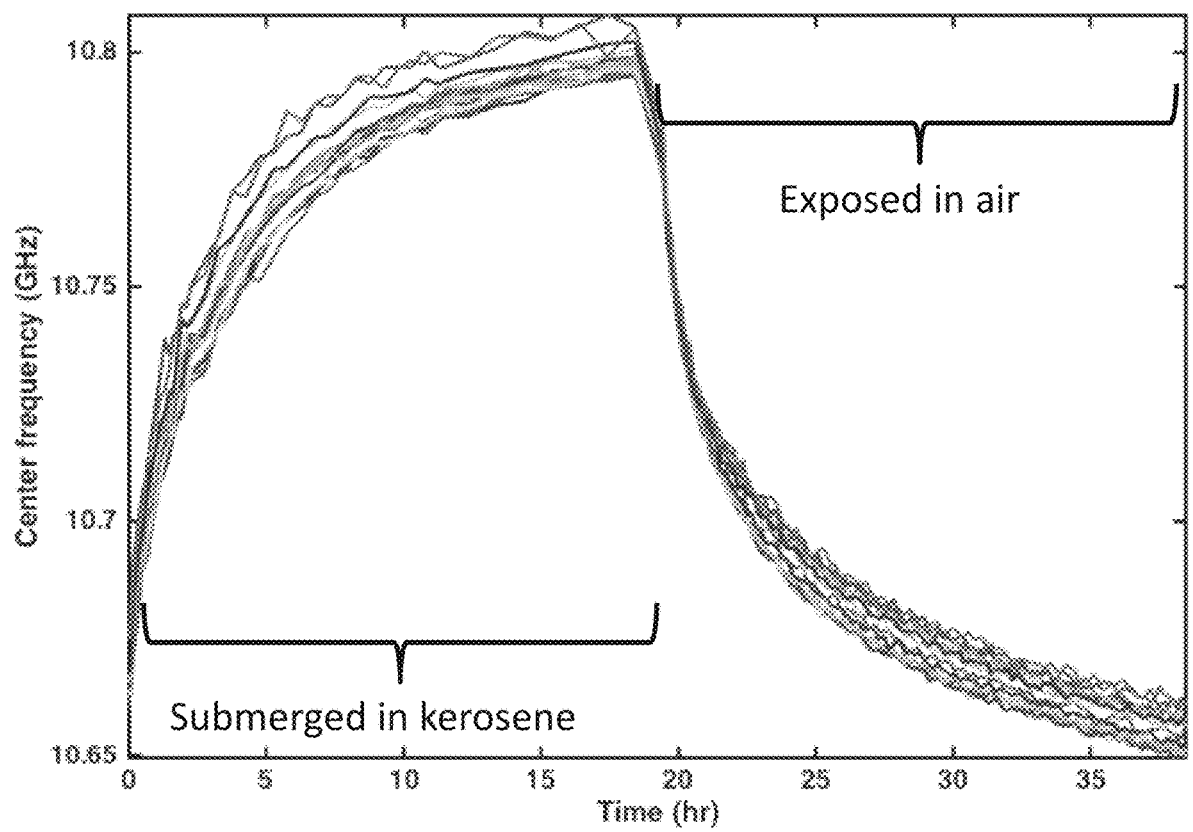
FIG. 3C is a line graph depicting the strain in the optical fiber over time during exposure to a hydrocarbon and after discontinuation of the exposure to the hydrocarbon. The different lines represent different positions along the length of the sensing cable.
Figure 3D:
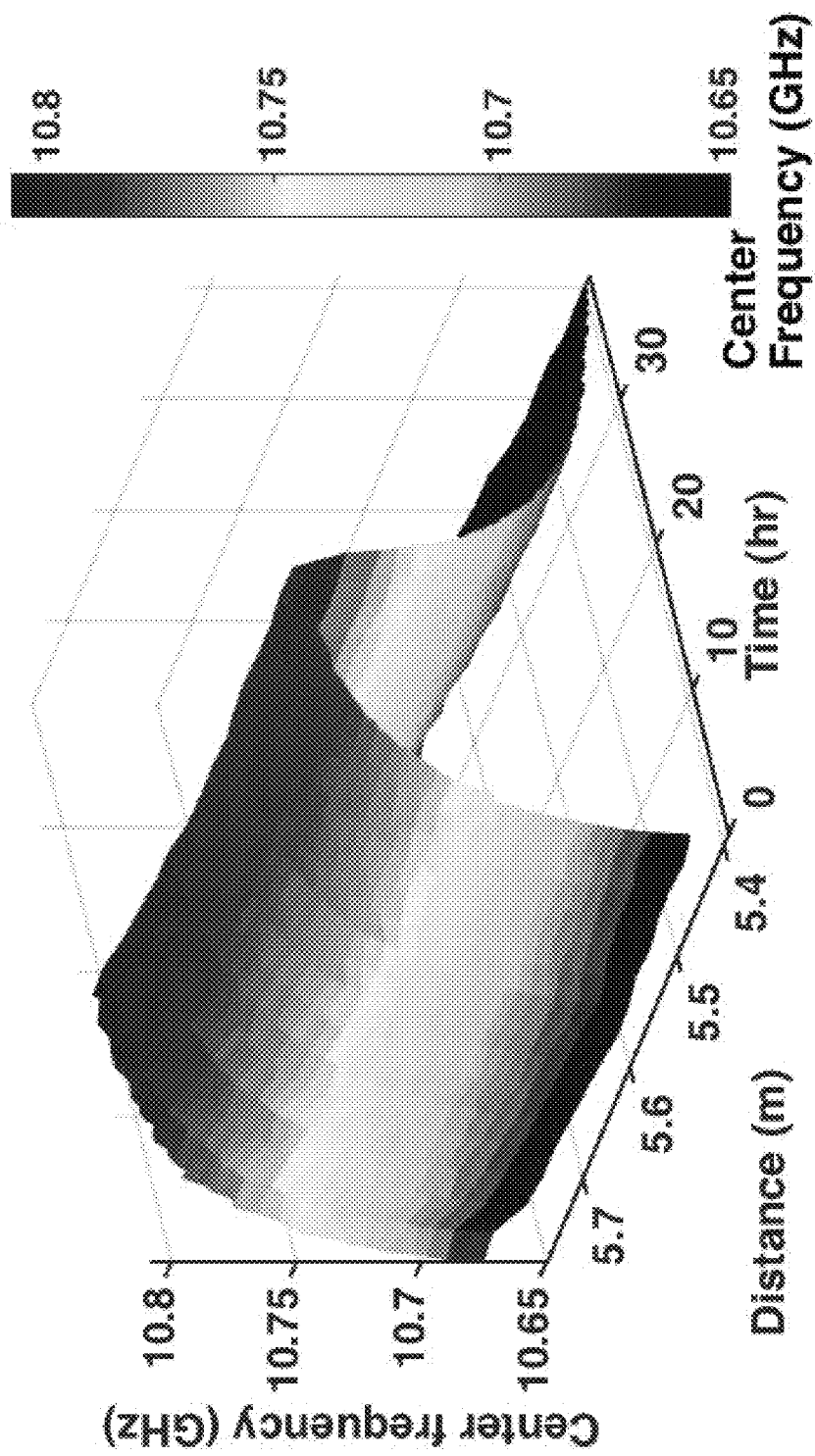
FIG. 3D is a three-dimensional graph depicting the strain in the optical fiber over time during exposure to a hydrocarbon and after discontinuation of the exposure to the hydrocarbon, along the length of the sensing cable.

The presence of hydrocarbons caused the hydrocarbon-sensitive polymer around the optical fiber to swell, leading to changes in strain on the optical fiber. These strain variations were detected using the DTSS monitoring system. FIG. 2 shows the central frequency of the optical fiber as a function of the time of exposure to the hydrocarbon. Each line of the graph shows the strain at a different point along the length of the fiber. FIG. 3A shows an optical fiber 3 bound to a hydrocarbon-sensitive polymer 5 that has been submerged in kerosene. FIG. 3B shows the same setup three days after removal from the kerosene, wherein the swelling of the polymer has decreased, reducing the strain on the optical fiber. This is shown graphically in FIGS. 3C and 3D. The different lines of FIG. 3C represent different points along the length of the fiber. FIG. 3D particularly demonstrates that the effect of the hydrocarbon is measurable (and that the strain behavior is uniform) along the entire length of the optical fiber.

Figure 4A:
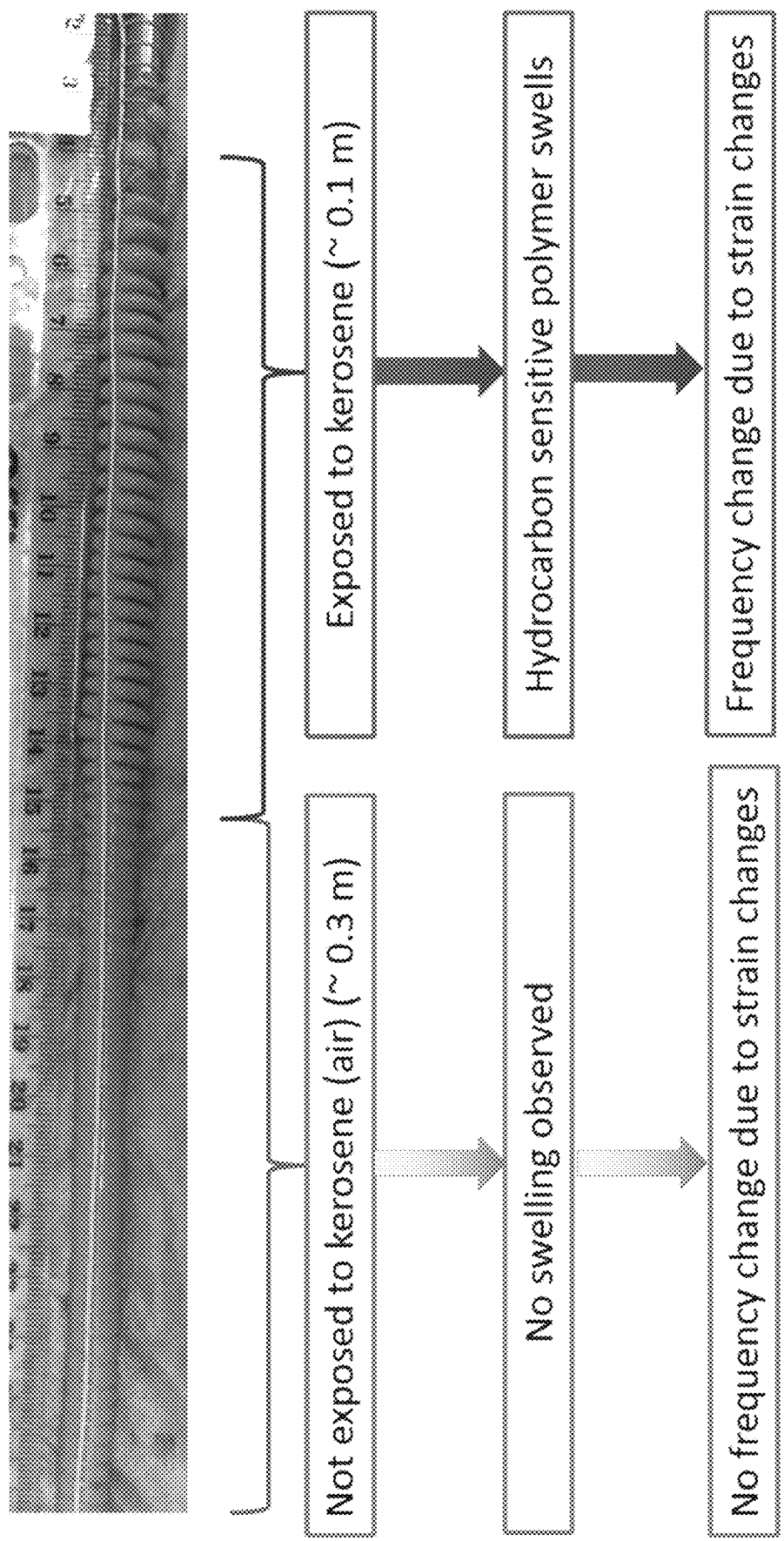
FIG. 4A is a photograph showing a sensing cable that has been exposed to a hydrocarbon along only certain portions of its length.
Figure 4B:
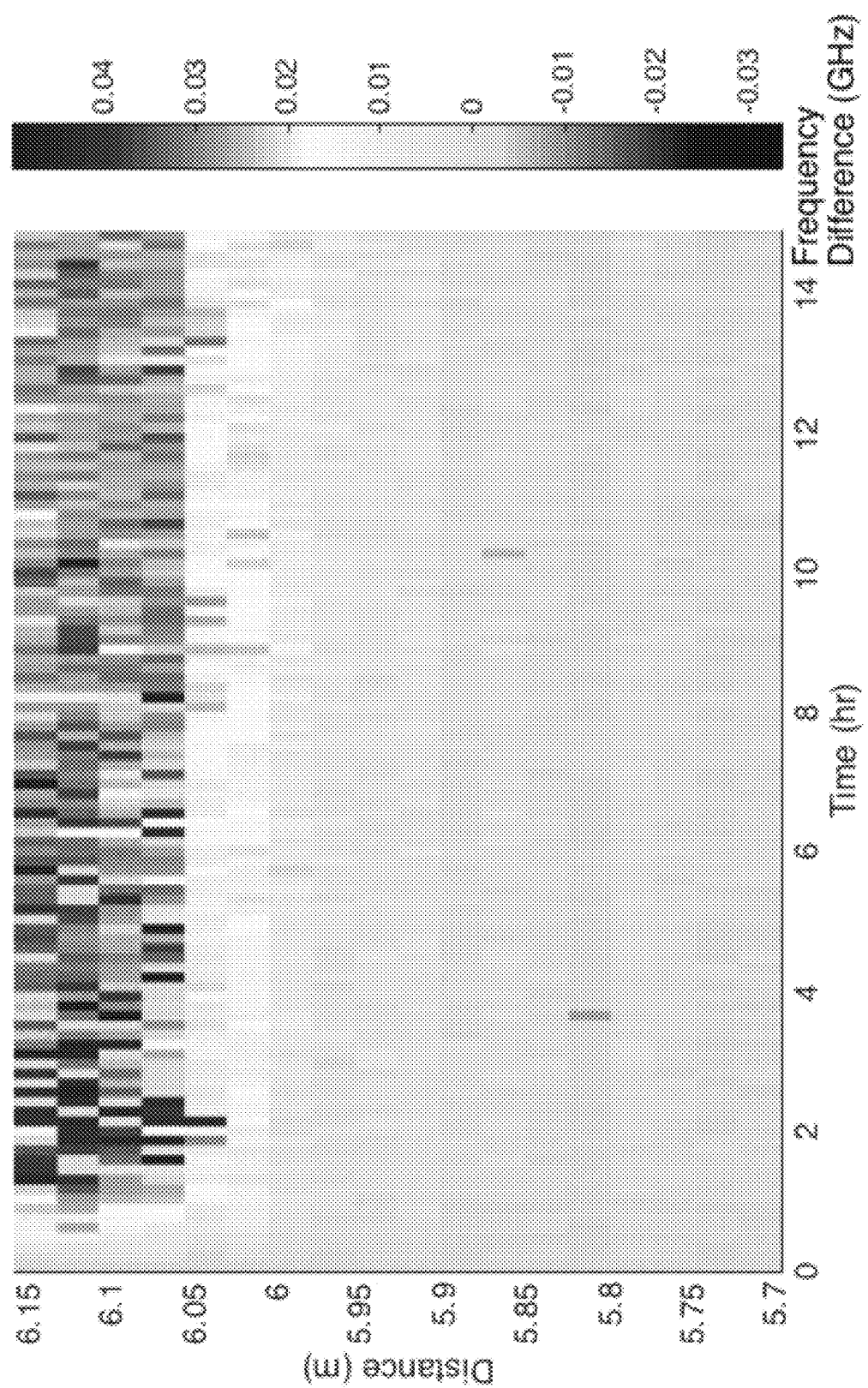
FIG. 4B is a heat map showing the frequency variation before and after exposure to the hydrocarbon and at various points along the length of the sensing cable.

The sensing cable 1 can also detect variations in hydrocarbon exposure along its length. FIG. 4A shows a cable (outer sheath not present) in which the right side has been exposed to kerosene and the left side has not. The polymer material 5 on the right side is swollen against the attached optical fiber 3. The strain induced by the swelling is detected, as well as the position of that strain along the length of the fiber 3. The region exposed to the kerosene displays a frequency difference, as shown in FIG. 4B.

The observed strain variations were found to be dependent on the type of hydrocarbons. For example, synthetic based mud (SBM) which is frequently used as a non-aqueous drilling fluid and is typically based on a synthetic based fluid (olefin, paraffin, ester or a combination thereof) had little effect on the strain, while kerosene showed a significant response.

In addition to detecting hydrocarbons, the DTSS system was also used to monitor heat evolution during cement hydration. Incomplete displacement of SBM with cement leads to contamination of cement, which in-turn causes a decrease in the amount of heat that is evolved during cement hydration. These changes in the heat signal were detected by the DTSS system. This is highly relevant information because contamination of cement is one of the main factors that negatively impacts primary cementation by weakening the cement, making it susceptible to cracking and hydrocarbon invasion thus compromising zonal isolation.

In combination of detecting hydrocarbon and monitoring cement hydration process, the system also presents a solution for monitoring the cement displacement process. The cable responds to SBM and spacer fluid with strain values in different orders of magnitude, which can be used to track each of these fluids during the displacement process in real time. Note that the behavior of the cable exposed to spacer fluid can be altered to generate a specific response by adding tracers. After the cement slurry is pumped in place, the strain and temperature measurement obtained from the DTSS system can be used to track the displacement process and the location of the cement slurry.

In conclusion, this DTSS system can be beneficial in many situations, including but not limited to: monitoring cement displacement process, evaluating the state of primary cementation, monitoring any unwanted hydrocarbon migration in the cement sheath, identifying zones from which hydrocarbons are originating and providing other essential information to identify the need for well intervention, such as remedial cementing. Existing sensor techniques require active re-entry into the well using drillpipe or wireline to deploy sensors and logging tools. The proposed monitoring system can provide real-time, continuous, lifetime and non-destructive monitoring of the state of zonal isolation; without costly and time-consuming entry into the well. This technique also provides a method to detect connected channels that provide paths for hydrocarbons.

What is claimed is:
1. A system for monitoring cement integrity in a downhole environment, the system comprising:
   a sensing cable, the sensing cable comprising:
      an optical fiber comprising a hydrogen darkening-resistant material, wherein the optical fiber is a single mode optical fiber,
      a hydrocarbon-sensitive polymer that undergoes a change in a degree of swelling in a presence of hydrocarbons, and
      a protective outer sheath surrounding at least a portion of the optical fiber and the hydrocarbon-sensitive polymer; and
   cured cement in the downhole environment, the sensing cable encased within the cured cement in the downhole environment,
   wherein a first attachment mechanism is positioned around the optical fiber and an outer surface of the hydrocarbon-sensitive polymer such that the change in the degree of swelling of the hydrocarbon-sensitive polymer produces a change in a measurable property of the optical fiber, wherein the protective outer sheath is secured to the optical fiber by a second attachment mechanism, wherein the first attachment mechanism is under the protective outer sheath, and wherein the second attachment mechanism is over the protective outer sheath.
2. The system of claim 1, wherein the optical fiber is configured to separate strain and temperature measurements.
3. The system of claim 1, wherein the hydrogen darkening-resistant material is a pure silica core, a fluorine-doped silica core, or a carbon coating.

4. The system of claim 1, wherein the optical fiber is configured to simultaneously provide strain and temperature measurements.

5. The system of claim 1, wherein the hydrocarbon-sensitive polymer comprises natural rubber or synthetic rubber.

6. The system of claim 1, wherein the hydrocarbon-sensitive polymer comprises silicone rubber, butyl rubber, EPDM rubber, or a combination thereof.

7. The system of claim 1, wherein the measurable property is a strain of the optical fiber.

8. The system of claim 1, wherein the hydrocarbon-sensitive polymer is in direct contact with the optical fiber.

9. The system of claim 1, further comprising a packaging configured to reinforce the optical fiber.

10. The system of claim 9, wherein the packaging comprises a reinforcement rod.

11. The system of claim 1, further comprising an intermediate material positioned between the hydrocarbon-sensitive polymer and the optical fiber.

12. The system of claim 1, wherein the protective outer sheath comprises a steel braid.

13. The system of claim 10, wherein the reinforcement rod comprises fiberglass or steel.

14. The system of claim 13, wherein the hydrocarbon-sensitive polymer surrounds the reinforcement rod.

15. The system of claim 1, wherein the-optical fiber is attached to the outer surface of the hydrocarbon sensitive polymer by the first attachment mechanism, the first attachment mechanism comprising a helically wound Kevlar thread.

16. The system of claim 1, wherein the second attachment mechanism is a helically wound Kevlar thread.

17. A method of assessing cement integrity in a downhole environment in real time, the method comprising:
attaching to a casing a sensing cable comprising:
an optical fiber comprising a hydrogen darkening resistant material,
a hydrocarbon-sensitive polymer that undergoes a change in a degree of swelling in a presence of hydrocarbons, wherein a first attachment mechanism is positioned around the optical fiber and an outer surface of the hydrocarbon-sensitive polymer such that the change in the degree of swelling of the hydrocarbon-sensitive polymer produces a change in strain of the optical fiber, and
a protective outer sheath surrounding at least a portion of the optical fiber and the hydrocarbon-sensitive polymer, the protective outer sheath secured to the optical fiber by a second attachment mechanism, wherein the first attachment mechanism is under the protective outer sheath, and wherein the second attachment mechanism is over the protective outer sheath,
positioning the casing in the downhole environment;
filling an annulus between the casing and a wall of the downhole environment with cement to encase the at least one sensing cable within cured cement in the downhole environment; and
monitoring a strain of the optical fiber and a temperature of the optical fiber to identify a change in an integrity of the cement, wherein monitoring includes simultaneously determining the strain and the temperature of the optical fiber by detecting scattered light using a hybrid Brillouin-Rayleigh detection method.

18. The method of claim 17, wherein the hybrid Brillouin-Rayleigh detection method uses the optical fiber for detecting the strain and the temperature of the optical fiber.

19. The method of claim 17, wherein the sensing cable further comprises a second hydrogen-darkening resistant optical fiber, and wherein the method further comprises measuring a temperature of the downhole environment with the second hydrogen-darkening resistant optical fiber.

20. The method of claim 17, wherein monitoring includes determining the strain of the optical fiber and the temperature of the optical fiber at multiple different downhole locations.

21. The method of claim 17, further comprising assessing zonal isolation using the strain of the optical fiber, the temperature of the optical fiber, or both.

22. The method of claim 17, wherein the optical fiber comprises a single mode optical fiber.

23. The method of claim 17, wherein the monitoring occurs over periods of time sufficient to monitor a quality of a well abandonment.

24. The method of claim 17, wherein the monitoring occurs continuously.

25. The method of claim 17, further comprising detecting hydrocarbon migration through the cement using the strain of the optical fiber, the temperature of the optical fiber, or both.

26. The method of claim 25, further comprising identifying zones from which hydrocarbons are originating using the strain of the optical fiber, the temperature of the optical fiber, or both.

27. The method of claim 25, further comprising detecting connected channels that provide paths for hydrocarbon migration using the strain of the optical fiber, the temperature of the optical fiber, or both.

28. The method of claim 25, further comprising undertaking remedial cementing after identifying zones from which hydrocarbons are originating.

29. The method of claim 17, further comprising evaluating a state of primary cementation.

30. The method of claim 29, wherein evaluating the state of primary cementation comprises monitoring heat evolution during cement hydration with a hydrogen darkening-resistant optical fiber.

31. The method of claim 17, further comprising detecting contamination of the cement with drilling fluids by detecting variation in the strain of the optical fiber, the temperature of the optical fiber, or both.

32. The method of claim 17, further comprising differentiating between different types of hydrocarbon-based contaminants by distinguishing a degree to which the strain of the optical fiber is changed.

33. The method of claim 17, wherein the optical fiber is a quasi-distributed optical fiber.

34. The method of claim 33, wherein the quasi-distributed optical fiber comprises a fiber Bragg grating.

35. The method of claim 17, wherein the optical fiber is a distributed optical fiber.

36. The method of claim 17, further comprising attaching one or more additional sensing cables to the casing.

37. The method of claim 36, wherein the sensing cable and the one or more additional sensing cables are oriented vertically along the casing.

38. The method of claim 36, wherein the sensing cable and the one or more additional sensing cables are arranged in helical configurations around the casing.

39. The method of claim 38, wherein the helical configurations of the sensing cable and the one or more additional sensing cables are the same.

40. The method of claim 38, wherein the helical configurations of the sensing cable and the one or more additional sensing cables are different.

41. The method of claim 17, wherein the monitoring includes using a surface read-out machine to measure the strain of the optical fiber.

42. The method of claim 41, wherein the surface read-out machine is a hybrid Brillouin-Rayleigh distributed fiber optic sensing system.

* * * * *